(12) United States Patent
Watson

(10) Patent No.: US 9,283,250 B2
(45) Date of Patent: Mar. 15, 2016

(54) ORAL ADMINISTRATION OF ELECTROLYZED WATER FOR TREATMENT AND PREVENTION OF PEDV IN SWINE, SWINE HERDS AND SWINE CONFINEMENTS

(71) Applicant: Robert D. Watson, Fort Madison, IA (US)

(72) Inventor: Robert D. Watson, Fort Madison, IA (US)

(73) Assignee: Ag Odor Control, LLC, Ft. Madison, IA (US)

( * ) Notice: Subject to any disclaimer, the term of this patent is extended or adjusted under 35 U.S.C. 154(b) by 165 days.

(21) Appl. No.: 14/188,231

(22) Filed: Feb. 24, 2014

(65) Prior Publication Data

US 2014/0287065 A1   Sep. 25, 2014

Related U.S. Application Data

(60) Provisional application No. 61/783,280, filed on Mar. 14, 2013.

(51) Int. Cl.
*A61K 33/20* (2006.01)
*A61K 33/00* (2006.01)

(52) U.S. Cl.
CPC ............ *A61K 33/20* (2013.01); *A61K 33/00* (2013.01)

(58) Field of Classification Search
None
See application file for complete search history.

(56) References Cited

U.S. PATENT DOCUMENTS

| | | | | |
|---|---|---|---|---|
| 3,898,328 A * | 8/1975 | Beigler | A61K 33/00 | 424/601 |
| 4,652,454 A * | 3/1987 | Remesy | A23C 11/04 | 426/583 |
| 4,839,347 A * | 6/1989 | Franz | A61K 33/00 | 426/801 |
| 4,857,338 A * | 8/1989 | Ybema | A23K 1/08 | 426/2 |
| 5,008,248 A * | 4/1991 | Bywater | A61K 31/7004 | 424/442 |
| 5,028,437 A * | 7/1991 | Jerrett | A61K 31/7004 | 424/535 |
| 5,038,396 A * | 8/1991 | Gjerlov | A61K 36/68 | 424/601 |
| 5,089,477 A * | 2/1992 | Fregly | A23L 1/304 | 424/601 |
| 2004/0131695 A1* | 7/2004 | Hinze | A61K 33/00 | 424/600 |
| 2006/0004072 A1* | 1/2006 | Howarth | A01N 43/50 | 514/389 |
| 2012/0156307 A1* | 6/2012 | Chen | A01N 59/00 | 424/600 |

FOREIGN PATENT DOCUMENTS

RU   2196591 C1 *   1/2003

OTHER PUBLICATIONS

Abstract of RU 2196591 C1 (Shkil et al.). Derwent World Patents Index Accession No. 2003-478504 (published Week 45 of 2003).*
"Porcine Epidemic Diarrhoea." _WikiVet_. Last modified on Dec. 22, 2011. Archived on Apr. 1, 2012 by the Wayback Machine. _Internet Archive_. https://web.archive.org/web/20120401132621/http://en.wikivet.net/Porcine_Epidemic_Diarrhoea].*
Weber, Olaf, and Axel Schmidt. "Coronavirus infections in veterinary medicine." Coronaviruses with Special Emphasis on First Insights Concerning SARS. Birkhäuser Basel, 2005. 55-69.*
Saif, Linda J. "Comparative pathogenesis of enteric viral infections of swine." Mechanisms in the Pathogenesis of Enteric Diseases 2. Springer US, 1999. 47-59.*
Song, Daesub, and Bongkyun Park. "Porcine epidemic diarrhoea virus: a comprehensive review of molecular epidemiology, diagnosis, and vaccines." Virus genes 44.2 (2012): 167-175.*
Haydon, K. D., and J. W. West. "Effect of dietary electrolyte balance on nutrient digestibility determined at the end of the small intestine and over the total digestive tract in growing pigs." Journal of animal science 68.11 (1990): 3687-3693.*

* cited by examiner

*Primary Examiner* — Bethany Barham
*Assistant Examiner* — Peter Anthopolos
(74) *Attorney, Agent, or Firm* — Camille L. Urban; David M. Breiner

(57) ABSTRACT

Pigs infected with PEDv often die due to dehydration caused by diarrhea. Those that survive do not reach market weight as scheduled resulting in costs to the producer. The invention includes providing electrolyzed water either as treatment for infected animals or as a prophylactic against symptom severity in uninfected animals. The electrolyzed water is used as a substitute for or as a solution with regular drinking water. Duration of symptoms for infected pigs is markedly lessened; severity of symptoms is also reduced providing a much higher survival rate. Time to market is less negatively affected for surviving pigs than those untreated, and weight at scheduled time for sale is also less effected translating into positive financial results over those expected for untreated herds.

16 Claims, No Drawings

ORAL ADMINISTRATION OF ELECTROLYZED WATER FOR TREATMENT AND PREVENTION OF PEDV IN SWINE, SWINE HERDS AND SWINE CONFINEMENTS

This application claims priority of U.S. Provisional Application No. 61/783,280 filed with the US Patent and Trademark Office on Mar. 14, 2013, the entire contents of which is herein incorporated by reference.

FIELD OF THE INVENTION

The present invention relates to animal husbandry practices in general and, more specifically, to a method for preventing certain diseases and alleviating symptoms of certain disease states, particularly those resulting from PEDv, resulting in improved health of the animal.

BACKGROUND OF THE INVENTION

Electrolyzed water including its characteristic ions may be formed by one of several ways. One of the several ways comprises adding a small amount of sodium chloride (NaCl) to pure distilled water, and conducting a current through it across an anode and a cathode. The cathode area attracts the sodium ion and produces basic water, while the anode area attracts the chlorine ion and produces acidic water. In this process, hydrogen gas and hydroxide ions are produced at the cathode, leading to an alkaline solution that consists essentially of sodium hydroxide. At the anode, chloride ions are oxidized to elemental chlorine. If some of this chlorine is allowed to combine with some of the hydroxide ions produced at the cathode, it disassociates into hypochlorous acid, a weak acid and an oxidizing agent. The "acidic electrolyzed water" can be raised in pH by mixing in the desired amount of hydroxide ion solution from the cathode compartment, yielding a solution of sodium hypochlorite NaClO which is the major component of ordinary household laundry bleach. For example, a solution whose pH is 7.3 will contain equal concentrations of hypochlorous acid and hypochlorite ion; reducing the pH will shift the balance toward the acid.

Because electrolyzed water may have a short shelf life depending on the method by which it is made and several other factors, the widespread use and production of electrolyzed water have been impractical and somewhat unfeasible. Electrolyzed water has been certified for medical use in Japan since the mid-1980s. Most often, it is sold and used in either the basic form or the acidic form.

The first type of electrolyzed water which was used was the acidic type, which was accepted quickly by the Japanese food industry. It was useful for killing bacteria and parasites in raw fish without compromising its quality. Alkaline water was developed next, and it was used in hospitals to alkalize the body and as an "energy enhancer".

Diseases in animal herds have always been problematic for herdsmen. Although diseases and health problems occurred when animals such as swine, cattle, chickens, and horses were reared mostly outdoors, since the advent of confined growth and production of these animals in confinements housing hundreds of animals, the incidence, threat and spread of disease has increased astronomically. The negative effects of disease are magnified by the speed with which contamination can spread both within and between confinements.

It has long been known that disease often travels via animal to animal contact, perhaps through shared watering or feeding equipment and container or via airborne transfer. It is also theorized—and in some cases known—that air quality in general may affect the overall health, feed to gain ratio, or feed intake of the animals in addition to exacerbating symptoms of certain disease states.

Some disease examples that plague producers of swine and are related in some way to environmental transmission include the following, several of which include symptoms that may be reduced or contamination that may be mitigated by the uses of electrolyzed water as taught by the current invention:

Arthritis: Arthritis can cause heavy losses of hogs. The disease may result from a variety of causes including Streptococcus bacteria, erysipelas and injury. It is thought that keeping hogs on damp, cold or rough surfaces may contribute to arthritis. Symptoms include lameness, swollen, hardened joints and stunted growth. Arthritis is treatable with antibiotics if caught in the early stages and there are vaccines for arthritis caused by erysipelas and Streptococcus.

*Bordatella Rhinitis* is caused by an infection of the nasal cavity of hogs by *Bordatella bronchiseptica*, an organism that gets onto open scratches or wounds in the nose or mouth. It can be transmitted from sow to piglet. Symptoms include sneezing and a general failure to thrive. Treatment with antibiotics may be effective. A vaccine is available.

Circovirus: Porcine Circovirus Disease (PCVD) or Circo is a viral disease that has become a major problem in the United States. Caused by Porcine Circovirus Type 2 (PCV2), not all pigs develop clinical signs of the disease but most swine are infected. Symptoms, duration and mortality can vary by herd. Symptoms can include enlarged lymph nodes, skin rashes, difficulty breathing, jaundice, fever, stomach ulcers and diarrhea. Risks include poor growth, weight loss and weakness with increased chance of mortality between 5 to 14 weeks. There is a vaccine available.

*Clostridium Enteritis*: This disease is found among piglets less than a week old and is caused by the bacterium *Clostridium perfringens* Type C. Symptoms include yellow, pasty diarrhea, weakness and trying to be near a warm place. It is spread through piglet to piglet contact and infected feces of the sow. Treatment with antibiotics is possible, but most survivors will be permanently stunted. Vaccination is available for pregnant sows and gilts prior to farrowing.

Erysipelas: This very common hog disease is caused by the bacterium *Erysipelothrix Rhusiopathiae*, found in almost every pig farm. Up to half of animals carry it. It is nearly always present in the pig environment and spreads through saliva, feces or urine. It comes on suddenly. It is most often caused by poor hygiene. Treatment is penicillin. A vaccine is available to be given at 3 weeks of age and older.

Flu: Swine Influenza Virus can be passed by infected pigs, birds or humans. This disease can be dramatic with a rapid onset in 12 to 48 hours. Symptoms include coughing, fever, loss of appetite and pneumonia. Infertility can result in sows and the high fevers can cause abortions. Vaccination is available.

Greasy Pig Disease: The disease is caused by the bacterium *Staphylococcus hyicus* which lives normally on the skin without causing disease. This bacterium is normally present on the skin, but in the disease state the bacterium causes dermatitis and oozes greasy fluid. The toxins produced are absorbed and can damage the liver and kidneys. In the sucking piglet disease is usually confined to individual animals, but it can be a major problem in new gilt herds and weaned pigs. Treatment includes antibiotics, disinfecting by washing the infected skin, and disinfecting the confinement and crates after a litter is emptied.

Ileitis: A common ailment in swine of all ages and especially in pigs that have been recently weaned. Symptoms include inflammation of the small and/or large intestine, diarrhea and stomach distress. Stress is often listed as a cause for this illness. Vaccination through drinking water is available.

Leptospirosis: Caused by the bacterium *Leptospira*. Symptoms include loss of condition and reproduction problems. It's difficult to eradicate once started as it spreads by mouth, urine, wallows, feed, water, venereal transmission and contaminated surfaces. Treatment with antibiotics is recommended; there is also a combination vaccine available.

Mycoplasmal Pneumonia: Symptoms include coughing and difficulty breathing. Caused by bacteria and highly contagious, it can be spread by air, contaminated surfaces, pig to pig, feed and water. Treatment with antibiotics is recommended; vaccination is available.

PEDv: (Porcine Epidemic Diarrhea Virus): Introduced into the US from elsewhere this virus appeared in multiple, widely distributed sow herds within days, implying a common point-source origin. The virus in the US is 99.4% homologous with that in China in 2012, it has spread to 20 states as of this date, and producers can expect losses of up to 100% of piglets 3 weeks and less of age. Present recommendations for management of infection include fully infecting the herd to accomplish immunity. Infected pigs exhibit symptoms such as watery diarrhea for a week to 10 days before recovering. The incubation time of the disease from contact to symptomatic is thought to be between about 22 and 36 hours; 2-4 days at herd level. Neonatal pigs in a farrowing unit often experience death rate at 100%. In general, the younger the animals the higher the risk of death. In hog production operations, the virus can spread rapidly and cause increase in costs and time to production at best, and, at worst, death rates that can be debilitating for the producer. Almost always, pigs that have suffered PEDv and survived will be sold at measurably lighter weights in order to clear the confinement on schedule, costing the producer thousands of dollars. It is believed that PEDv (and its major symptom) negatively affects feed to gain ratios.

Porcine Parvovirus: This one is probably the most common cause of infectious infertility in hogs. There are rarely any clinical symptoms except stillbirths, mummified piglets and small litters due to loss of embryos in the womb. Unlike most viral infections, Porcine Parvovirus can live in soil and on surfaces for months. It's resistant to most disinfectants. Once a pig has had it, there is a lifelong immunity. There is no treatment, but vaccine is available.

PRRS: Porcine Reproductive & Respiratory Syndrome. Production losses can be attributed to reduction in farrowing rate, reduced number of live births/increased stillbirths, poor reproduction in gilts and early farrowing. Symptoms include a reluctance to drink, loss of appetite in sows at farrowing, blueing of the ears, respiratory signs and coughing, no milk and lethargy. This disease first classified in 1991. Vaccine is available.

Rotavirus: Rotavirus is widespread in almost all pig populations. Symptoms include diarrhea, dehydration, sunken eyes and wasting. Rotavirus is usually caused by poor hygiene, temperature fluctuations and contaminated boots and clothing. Vaccine is available.

Scours (*E, coli/Clostridium perfringens* type C): Scours or baby pig diarrhea is the most common disease among baby pigs. While scours can occur at any age during nursing, there are often two peak periods—before 5 days and between 7 and 14 days. Scours causes severe production losses as well as substantial death losses. Vaccination is available for pregnant sows and gilts prior to farrowing.

TGE: Transmissible gastroenteritis (TGE) in swine is known to be one of the most significant diarrhea-producing diseases in young pigs. The TGEV is vulnerable to sunlight and various disinfectants such as sodium hypochrolite or iodines. It causes high morbidity/mortality in pigs less than two weeks of age. Many pigs older than three weeks of age will survive but are likely to remain stunted. Anti-biotic treatment is not indicated; vaccine is not typically employed. Good biosecurity and cleaning is recommended.

About 140 diseases are listed at "www.thepigsite.com" including recommended treatments and preventative measures. In short, there are dozens of diseases and/or conditions that swine might suffer and nearly all of them are exacerbated by confinement growth. Further, there are many that include gastrointestinal symptoms such as diarrhea. Unchecked diarrhea can and does cause death and/or failure to thrive of thousands of hogs every year. By raising hogs in confinements, diseases causing such symptoms can spread through a herd in a matter of only a few days, can result in up to 100% death for neonatal piglets, and cause high rates of death in grow finish operations as well as sows.

Cattle diseases of interest include, but are not limited to, the following:

Clostridial diseases caused by bacteria are blackleg, red water, enterotoxemia and tetanus. Sudden death is often the first and only sign of these cattle diseases.

Respiratory diseases or BRD also known as "shipping disease" or "shipping fever" are the costliest of all cattle diseases, resulting in poor gains and a weakened immune system. Coughing, nasal discharge, fever and difficulty breathing are among the symptoms of these cattle diseases.

Scours or diarrhea is a common cattle disease that often affects baby calves. Animals that survive this cattle disease often remain weak and perform poorly throughout their lives.

Although cattle are more often raised outdoors, a number of the aforementioned diseases might be addressed by ingestion through common watering equipment, or by topical treatment of animals, if a substantially whole body treatment regime could be devised. And it would be desirable to reduce infection and transmission that occurs by contamination of water containers, equipment or barn interiors.

Although vaccine and/or treatment for many of the most common communicable or environment specific diseases of swine, cattle and poultry have been developed, it is not feasible to administer all vaccines to a single animal. The vaccines come with an economic price as well as a cost in labor and effort. They are often not immediately effective and, therefore, may be a wholly unnecessary cost for a herd that is never exposed. More importantly, many common diseases can be prevented through a solid program of good hygiene and animal husbandry, control of flies and biting insects, and selective vaccination when possible and feasible. Some cattle diseases might be addressed by body surface treatment, through watering facilities, or, where barns or other confinement arrangements are employed, good hygiene and animal husbandry may have a positive effect. Many poultry diseases and swine diseases may, likewise, be addressed by hygiene or treatment protocols for the confinement and its atmosphere.

What was needed was a simple, inexpensive, and effective means to improve air quality in animal confinements and reduce symptoms of respiratory and gastrointestinal diseases. Further, for animals outdoors there was a need for a full body treatment to reduce presence of certain viral or bacterial load on the animal's skin and/or fur for reduction of the rate of transmission and infection.

A first objective of the present invention was to provide a means to reduce viral or bacterial load on surfaces or in the air;

A second objective of the present invention was to provide a means to reduce symptoms of respiratory distress or other causes of animal distress associated with disease state or poor air quality;

A third objective of the present invention was to provide a simple means to reduce bacterial load for livestock;

A fourth objective of the present invention was to provide means to administer an anti-viral or anti-bacterial to livestock via respiratory therapy;

A fifth objective of the present invention was to provide means to reduce virus and bacterial levels on the skin or fur of infected or carrying animals;

A sixth objective of the present invention was to provide means to reduce dehydration of a diseased animal;

A seventh objective of the present invention was to provide an oral treatment, easily administered, for the management of the symptoms associated with PEDv or TEG, predominantly watery diarrhea and ensuing dehydration;

An eighth objective of the present invention was to provide an oral treatment, easily administered, for reducing the days to recovery and to minimize weight loss of an animal infected with PEDv in order to generally preserve life, time to market, and feed to gain ratio;

A ninth objective of the present invention was to provide a method for reducing risk and recovery time during intentional exposure of a herd to PEDv.

A tenth objective of the present invention was to provide a method for full herd exposure to reach endemic status and full immunity while at the same time minimizing loss of life, reducing time to recovery, and reducing symptoms and their effects.

SUMMARY OF THE PRESENT INVENTION

The present invention delivers electrolyzed water, preferably but not necessarily near neutral pH or slightly basic, orally. The invention covers delivery of electrolyzed water, preferably near neutral pH or slightly basic, in liquid form for ingestion, typically administered through drinking water. As a matter of review of information well-known in the art, and not as a point of novelty:

In pure water electrolysis:

Cathode (reduction): $2 H_2O (l) + 2e^- \rightarrow H_2 (g) + 2 OH^- (aq)$

Anode (oxidation): $4 OH^- (aq) \rightarrow O_2 (g) + 2 H_2O (l) + 4 e^-$

Combining either half reaction pair yields the same overall decomposition of water into oxygen and hydrogen. Overall reaction: $2 H_2O (l) \rightarrow 2 H_2 (g) + O_2 (g)$ Addition of chlorine to water gives both hydrochloric acid (HCl) and hypochlorous acid (HClO): $Cl_2 + H_2O \rightleftharpoons HClO + HCl$ When chlorine is added to the water for electrolysis in the form of sodium chloride, the sodium salt of hypochlorous acid is formed. $NaCl + H_2O + electricity \rightarrow NaOCl + H_2$ This same general reaction occurs for several other salts when present during electrolysis of water.

When acids are added to aqueous salts of hypochlorous acid (such as sodium hypochlorite in commercial bleach solution), the resultant reaction is driven to the left, and chlorine gas is evolved. Thus, the formation of stable hypochlorite is facilitated by dissolving chlorine gas into basic water solutions, such as sodium hydroxide.

The oral delivery of electrolyzed water is intended to be used in confinements where animals such as swine and poultry are raised. Further, oral delivery in stables and barns where any animals such as horses, sheep, goats, and other animals are housed may be beneficial to the health of these animals, as well. Finally, oral administration through drinking water facilities, where present for outdoor herds, is also expected to have effect.

Animals suffering from disease states that cause gastrointestinal or respiratory symptoms, such as but not limited to PEDv or TEG, and to which electrolyzed water at or near pH neutral and slightly basic, for example, pH about 6 to about 9 or pH between about 7 and about 9, is orally administered recover much more effectively and quickly from these illnesses above than animals to which it is not administered. Their symptoms are reduced in severity and duration. Time to recovery is shortened. Feed to gain ratio is generally preserved or at least does not suffer to the degree of that of untreated animals and time to market can be mostly preserved. Yet, immunity comparable to untreated animals is achieved.

In the present invention, the fluid form of electrolyzed water is administered as drinking water or in certain concentrations in the drinking water for animals suffering the effects of a gastrointestinal disease such as PEDv or TEG. The benefits of ingesting electrolyzed water include improved hydration and lessening of symptoms such as diarrhea; reduction in symptomatic behavior such as lethargy, faster return to normal food intake, and reduction in time to recovery. For some disease states where electrolyzed water is both ingested and inhaled, benefits may be greater. The combined method of administration may show effects that are faster, or more dramatic, or both.

In another embodiment, the fluid form of electrolyzed water or the misted form may be used as a cleaning and/or rinsing agent on surfaces in the confinement or surfaces otherwise in contact with animals, for the equipment used with animals, and for the clothing worn by animal husbandry practitioners. Where a mist or vapor is administered, surface application is also accomplished, at least to a degree.

In another embodiment the fluid form or the misted form may be used to disinfect the skin and/or hair and/or feathers and/or fur of the animals to reduce viral or bacterial load thereon, for reducing rate of transmission and infection of the herd or group. Again, where a mist or vapor is administered, it is believed that animals present in the mist will benefit at least from a reduction of viral or bacterial load on the animal's skin, hair or fur. While there is a school of thought that advises infecting the whole herd to create immunity, surface disinfection is equally important, for minimizing transmittal of disease from farm to farm. Trailers, tires, boots, equipment, and vehicles can all be washed or soaked in the electrolyzed water as a means of minimizing or even eliminating viral transmissions.

In a final embodiment, the fluid form of electrolyzed water is combined with manure in a manure pit either by addition to the pit, or through addition along with the manure to the pit. For diseases primarily transmitted by oral fecal route, removal of manure and decontamination of it via application of electrolyzed water either prior to removal or after, will assist in minimizing transmission.

DETAILED DESCRIPTION OF THE PREFERRED EMBODIMENT

The present invention comprises application of electrolyzed water for the purpose of killing certain bacteria and viruses and for the purpose of decreasing gastrointestinal symptoms such as diarrhea and for increasing ease of breathing in animals suffering from a respiratory illness and alleviating other symptoms related to animal illness. Specifically in the present invention, electrolyzed water is employed for reducing severity of symptoms associated with PEDv such as diarrhea. The reduction of the severity of diarrhea lessens the degree of dehydration of the animal and lessens the time to recovery. This, in turn, can result in generally maintaining time to market and generally maintaining feed to gain ratio or at least providing an improvement compared to untreated animals. It is widely held that animals that die as a result of PEDv or become so sick as to never fully recover from PEDv do so mostly as a result of dehydration due to prolonged diarrhea. Therefore, alleviating this symptom can drastically improve the outlook for an infected animal, and an infected herd.

Example 1

As a method for alleviating symptoms of PEDv or TEG, electrolyzed water (typically, electrolyzed tap water and/or electrolyzed water where hypochlorous acid, sodium hydroxide, and sodium hypochlorite are present, ideally between about pH 6 and about pH 9, or between about 7.5 and 9, or between about pH 8 and about pH 9) was administered through drinking water. In tests, dilutions of drinking water between about 0.5% electrolyzed water and about 1.5% electrolyzed water in drinking water were provided to pigs in place of drinking water through the normal equipment employed for delivering drinking water.

Pigs under about 40 pounds were less likely to drink the higher concentrations; pigs above about 40 pounds drank the higher levels of concentrations. Adding more electrolyzed water is not expected to reduce its benefits and higher concentrations may be even more effective. Full strength electrolyzed water is nontoxic. However, it is suspected that certain animals are more sensitive to the taste of the higher concentrations of alkaline water and that it is less palatable to the animals. In order to obtain the benefit of the electrolyzed water, a certain amount of fluid needs to be ingested overall, along with the electrolyzed water. Therefore, where an animal is more sensitive to taste, resulting in less electrolyzed water being ingested, a lower dose may be used.

Example 2

In a first trial, pigs suffering from symptoms of PEDv at about 200 pounds were provided drinking water having about 1.5% electrolyzed water (typically, electrolyzed tap water and/or electrolyzed water where hypochlorous acid, sodium hydroxide, and sodium hypochlorite are present, ideally between about pH 6 and about pH 9, or between about 7.5 and 9, or between about pH 8 and about pH 9). About 48 hours after treatment via drinking water the diarrhea ceased. Within 1 week of beginning treatment, the pigs no longer tested positive for the disease. At 230 pounds these same pigs were again tested, and again all were negative.

Example 3

In a second trial, pigs ranging from about 7 pounds to about 45 pounds were treated after testing positive for PEDv and exhibiting classic symptoms including watery diarrhea and lethargy. These animals were provided drinking water comprising about 0.5% electrolyzed water. Within 48-72 hours the symptoms ceased. Observers noted the pigs also began acting normal rather than lethargic, and ate and drank normally. No deaths were reported in this group, even for the 7 pound young piglets.

Example 4

Drinking water in hog confinement when disease was present was supplemented with electrolyzed water at a rate of 40 gallons/210,000 gallons or about 1 gallon per about 525 gallons. The animals consistently drank more than in the nontreated confinements and symptom reduction was both faster and more pronounced.

Example 5

Cattle suffering from shipping fever were treated by irrigating nostrils with 10 cc's of electrolyzed water on day 1, and 5 cc's per day on days 2-5, and was added to drinking water. The symptoms cleared faster than in untreated animals and the transmission/infection rates were reduced.

Example 6

A 50% electrolyzed water solution was tested. The electrolyzed water was made by neutral electrolysis creating water with a pH of between about 7.5 and about 9. The solution killed *E Coli*, PRRS virus, *Staphylococcus aureus, Salmonella enterica* by contact. This solution, or one somewhat stronger or weaker, can be used as an electrolyzed water solution for a pre-soak or as a cleaning agent for barn turn over or crate cleaning, stall cleaning, and other cleaning purposes.

Example 7

Day 1 1st sign of PED appeared on one side of the confinement. Observed 1 pig scour. Started treatment of whole confinement same day. Treatment included replacing normal drinking water with electrolyzed water where hypochlorous acid, sodium hydroxide, and sodium hypochlorite are present, between about pH 8 and about pH 9.

Day 2 PEDv symptoms appeared in 6 more pens. But symptoms were not severe. Most pigs in pens that are affected still seem to be pretty clean. Roughly drank 8 gallons of treatment/pig. Animals appeared comfortable and not in distress.

Day 3 Do not see evidence of spread of virus to other pens. Seems that consumption of treated water spiked the first day and then gradually declined. Day 1 water increased 151 gallons. Day 2 dropped back 94 gallons/day. Day 3 dropped another 20 gallons.

Day 4 PED spread to 3 more pens. Most stools in pens were still solid. Pens that had PED initially (as observed on Day 2) now appear to be getting over the virus. Pigs look exceptionally good for day 3 after PED, No deads, No skinny. May want to consider 50/50 solution; treated barrel was not empty today. 100% solution may be too strong.

Day 5 Couple more (pens) broke today. Looks as though pens that broke on Day 2 are firming up. First 3-5 pens inside door on south side has gotten worse but everything else looks the same or a little better. Water consumption is going back up the last couple of days. (Total: 1 dead).

Day 6 about same as Day 5

Day 7 Looks as though it's almost cleared up. (Total: 1 dead).

Day 8 Pigs look good. Can't see any signs of PED.

In short, the treatment of all pigs, infected and uninfected, seemed to reduce both severity of symptoms and the duration of the disease dramatically from the statistical expectations. This experiment did not determine the rate of infection so it cannot be said whether the treatment reduced infection or just reduced the effects and appearance of the symptoms in animals that were infected.

Example 8

Treated Over the Course of Four (4) Days

Before Treatment: Before treatment the pigs were very inactive and un-responsive to a person being in the pen with them or to their mate, feeding and things of that sort. Pigs laid and acted very sick and weak.

Treatment; The treatment given to the pigs was a 50/50 mixture of the experimental product (electrolyzed water including hypochlorous acid, sodium hydroxide, and sodium hypochlorite) and normal drinking water which was provided to the pigs ad libitum in a canoe type gruel feeder. Treatment was given to the pigs for approximately 4 days. Water mixed with the experimental product was medicated water that had Pennchlor and Denguard in it. Size of the pigs that were treated varied from 10-20 lbs.

After Treatment; After the 4 day treatment the pigs seemed much better in the way they acted. They were eating and drinking more and were active and responsive when a person entered the pen with them. They looked as if they had put weight on and just acted healthier in general Example 9

An infected production facility, which was losing about 50 pigs per day to a PEDv outbreak, reported pigs lethargic and neither eating nor drinking in any measurable amounts. The barn was treated in the evening with a 50/50 solution of electrolyzed water and again at 4:00 am with full concentration. The hogs drank the treated water in quantity; no additional deaths occurred and the barn recovered in a matter of a few days.

Example 10

PEDv broke out in a production facility of 3000 head of hogs. The animals were scheduled to go to market just before Christmas. Became infected with PEDv before Thanksgiving; the producer was instructed to destroy the herd, On Thanksgiving Day the drinking water of the herd was dosed with 70 gallons of electrolyzed water, near neutral pH between about 7.5 and about 9, around 8.5. The symptoms of diarrhea disappeared in 48 hours.

The present invention has been described with specificity related to the use of electrolyzed water given orally for the relief of symptoms related to disease states; particularly effective with PEDv and other disease states for which diarrhea is a critical symptom. Although TGE may also be so treated, its effect is not quite as dramatic as pigs with TGE are reluctant to drink any water, with or without electrolyzed water diluted in it. Concentration of the electrolyzed water used in drinking water for the present invention may range from about 0.5% to about 100%, more preferably between about 0.5% and about 1.5%, up to about 50%. It is postulated that the lower concentrations are more palatable to the animals, especially the younger ones. The electrolyzed water may also be used as a solution for or pre-soak prior to cleaning surfaces with the expectation that certain important viruses such as PEDv and TGE and/or bacterial will be reduced or eliminated.

Finally, sanitizing surfaces in animal confinements through the use of foggers, misters, or sprayers where electrolyzed water is present in concentrations preferably above about 20%, and more preferably above about 50%, is within the purview of this invention.

Based on the data collected relative to the examples provided herein and qualitative data gathered by the inventors related to symptom relief in other animals, other disease states, using other concentrations of the solution, and different dosage regimes, the following claims are made. Although the invention has been described with particularity, one of ordinary skill in the art will be aware that the invention may be accomplished by the use of equivalents relative to steps, order of steps, application, concentrations, timing of dosages, duration of treatment or exposure, means of delivery, and other limitations present in the claims, all of which are within the scope of the invention as disclosed herein.

What I claim is:

1. A method for managing a plurality of pigs infected with PEDv, said method comprising providing to said plurality of pigs for drinking a solution comprising electrolyzed water and normal drinking water, said electrolyzed water comprising hypochlorous acid, sodium hydroxide, and sodium hypochlorite.

2. The method of claim 1 wherein providing said solution reduces the level of dehydration expected to be caused by PEDv infection.

3. The method of claim 1 wherein said electrolyzed water comprises pH between about 8 and about 9, and providing said solution reduces the duration of at least one of a plurality of symptoms caused by PEDv.

4. The method of claim 3 wherein one of said plurality of symptoms is diarrhea.

5. The method of claim 4 wherein another of said plurality of symptoms is dehydration.

6. The method of claim 3 wherein one of said plurality of symptoms is lethargy.

7. The method of claim 1 wherein said solution is between about 0.5% and about 1.5% electrolyzed water and providing said solution reduces the levels of dehydration and diarrhea expected to be caused by PEDv infection.

8. The method of claim 3 wherein said solution is between about 1% and about 50% electrolyzed water.

9. The method of claim 3 wherein said solution is between about 0.5% and about 100% electrolyzed water.

10. A method for managing a plurality of pigs infected with PEDv, said method comprising providing to said plurality of pigs for drinking electrolyzed water having hypochlorous acid, sodium hydroxide, and sodium hypochlorite, said electrolyzed water more highly concentrated in a solution with normal drinking water the first day of treatment than on subsequent days of treatment.

11. The method of claim 10 further comprising providing only electrolyzed water at full strength and no access to unelectrolyzed water to said plurality of pigs on the first day of treatment.

12. The method of claim 10 wherein after said first day of treatment said electrolyzed water may be provided in a solution with normal drinking water between about 0.5% and 50% electrolyzed water.

13. The method of claim 10 said electrolyzed water having pH between about 7 and about 9.

14. The method of claim 10 said electrolyzed water having pH between about 8 and about 8.8.

15. The method of claim 10 wherein the expected death rate of animals infected with PED is lowered.

16. The method of claim 10 wherein the expected death rate of animals infected with PED is lowered and said solution comprises between about 0.5% and about 50% electrolyzed water.

* * * * *